(12) United States Patent
Kumano

(10) Patent No.: US 10,145,376 B2
(45) Date of Patent: Dec. 4, 2018

(54) IMPELLER SHAFT TO BEARING INTERFACE FOR CENTRIFUGAL BLOOD PUMP

(71) Applicant: TERUMO KABUSHIKI KAISHA, Tokyo (JP)

(72) Inventor: Koko Kumano, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 355 days.

(21) Appl. No.: 15/082,291

(22) Filed: Mar. 28, 2016

(65) Prior Publication Data

US 2016/0208804 A1 Jul. 21, 2016

Related U.S. Application Data

(63) Continuation of application No. PCT/JP2014/083611, filed on Dec. 18, 2014.

(30) Foreign Application Priority Data

Dec. 27, 2013 (JP) .................................. 2013-272857

(51) Int. Cl.
*F04D 29/041* (2006.01)
*F04D 13/02* (2006.01)
(Continued)

(52) U.S. Cl.
CPC ......... *F04D 13/026* (2013.01); *A61M 1/1013* (2014.02); *A61M 1/3666* (2013.01);
(Continued)

(58) Field of Classification Search
CPC .. A61M 1/3666; A61M 1/1013; A61M 1/101; A61M 1/1006; F04D 13/026
See application file for complete search history.

(56) References Cited

U.S. PATENT DOCUMENTS

| 4,898,518 A | 2/1990 | Hubbard et al. |
| 5,399,074 A * | 3/1995 | Nose .................. F04D 29/0465 415/900 |

(Continued)

FOREIGN PATENT DOCUMENTS

| JP | 2006198272 A | 8/2006 |
| JP | 2012152315 A | 8/2012 |

(Continued)

OTHER PUBLICATIONS

European Patent Office, European Search Report, Reference MUB16-1150EP, Appln No. 14873355.3-1651/3088015 PCT/JP2014083611, dated Jun. 7, 2017.

*Primary Examiner* — Eldon Brockman
(74) *Attorney, Agent, or Firm* — MacMillan, Sobanski & Todd, LLC

(57) ABSTRACT

A centrifugal pump (10) includes a housing (26), an impeller (28) that is rotatably disposed inside the housing (26), a shaft (62) that has spherical surface-shaped shaft ends (66) at both ends in an axial direction, and bearings (70) that have spherical surface-shaped bearing surfaces (73) respectively and pivotally supporting the shaft ends (66). In at least one of the bearings (70) disposed on both sides of the shaft (62) in the axial direction, a ratio of a radius of curvature of the shaft end (66) with respect to a radius of curvature of the bearing surface (73) of the bearing (70) is equal to or less than 85%.

5 Claims, 6 Drawing Sheets

(51) Int. Cl.
  *F16C 17/08* (2006.01)
  *F04D 1/00* (2006.01)
  *A61M 1/36* (2006.01)
  *F04D 29/22* (2006.01)
  *A61M 1/10* (2006.01)

(52) U.S. Cl.
  CPC ............. *F04D 1/00* (2013.01); *F04D 29/041* (2013.01); *F04D 29/0413* (2013.01); *F04D 29/2255* (2013.01); *F16C 17/08* (2013.01); *A61M 1/101* (2013.01); *A61M 1/1006* (2014.02); *F16C 2240/70* (2013.01); *F16C 2360/44* (2013.01)

(56) References Cited

U.S. PATENT DOCUMENTS

| | | | | |
|---|---|---|---|---|
| 5,575,630 A * | 11/1996 | Nakazawa | ............ | F04D 13/026 415/900 |
| 5,713,730 A * | 2/1998 | Nose | ............ | F04D 29/0465 417/423.12 |
| 5,957,672 A * | 9/1999 | Aber | ............ | A61M 1/10 384/907.1 |
| 5,982,064 A * | 11/1999 | Umeda | ............ | F16C 21/00 310/61 |
| 6,254,359 B1 * | 7/2001 | Aber | ............ | F04D 3/02 417/356 |
| 6,884,210 B2 * | 4/2005 | Nose | ............ | A61M 1/1017 600/16 |
| 2003/0233021 A1 * | 12/2003 | Nose | ............ | A61M 1/1017 600/16 |

FOREIGN PATENT DOCUMENTS

| | | | |
|---|---|---|---|
| WO | 2007063843 A1 | 6/2007 | |
| WO | 2007063843 A1 | 7/2007 | |

\* cited by examiner

EXAMPLE

CONTROL 1

CONTROL 2

CONTROL 3

CONTROL 4

IMPELLER SHAFT TO BEARING INTERFACE FOR CENTRIFUGAL BLOOD PUMP

CROSS REFERENCE TO RELATED APPLICATIONS

This application is a continuation of PCT Application No. PCT/JP2014/083611, filed Dec. 18, 2014, based on and claiming priority to Japanese application no. 2013-272857, filed Dec. 27, 2013, both of which are incorporated herein by reference in their entirety.

TECHNICAL FIELD

The present invention relates to a centrifugal pump which delivers liquid such as blood and the like.

BACKGROUND ART

During cardiac surgery, a heart-lung machine is utilized. The heart-lung machine is used by being embedded in an extracorporeal circulation circuit and performs oxygenation of blood drained from a patient, and filtering for elimination of foreign bodies, and the like. There are various types of heart-lung machines (also known as perfusion systems) depending on differences such as the type of gas exchange unit, the type of pump, the position arrangement of pump, and the like. However, a heart-lung machine generally includes a reservoir (for venous blood), an oxygenator, a heat exchanger, a pump, and a plurality of tubes for connecting the components (for example, refer to JP-A-2009-160265).

One type of pump adapted for use in the heart-lung machine is a centrifugal pump which delivers blood by utilizing centrifugal force occurring due to rotations of an impeller. Generally, the centrifugal pump includes a housing, wherein the impeller is rotatably disposed inside the housing by a shaft which is provided at the center rotational axis of the impeller. A bearing on the housing rotatably supports the shaft. In order to reduce the occurrence of a thrombus (blood clot), a centrifugal pump may be used in which the bearing is formed as a pivot bearing.

In a case of the centrifugal pumps employing the pivot bearing, however, the occurrence of hemolysis (damage to blood corpuscles) may become more likely due to sliding between the shaft and the pivot bearing.

SUMMARY OF INVENTION

The present invention has been made in consideration of the foregoing problems, and an object thereof is to provide a centrifugal pump which can prevent hemolysis from being formed due to sliding between a shaft and a pivot bearing.

In order to achieve the object, according to the present invention, there is provided a centrifugal pump including a housing, an impeller that is rotatably disposed inside the housing, a shaft that is provided at a center rotation axis of the impeller having spherically-shaped ends at opposite axial ends, and bearings that have spherically-shaped bearing surfaces respectively to pivotally supporting the shaft ends. For at least one of the bearings, a ratio of a radius of curvature of the shaft end with respect to a radius of curvature of the bearing surface of the bearing is equal to or less than 85%.

According to the configuration of the present invention, a relationship between the radius of curvature of the shaft end of the shaft and the radius of curvature of the bearing surface of the bearing is set within the above-referenced range. Therefore, a gap between the shaft end of the shaft and the bearing surface of the bearing becomes suitable in size. Accordingly, it is possible to further reduce hemolysis from occurring due to sliding between the shaft and the bearing.

In the centrifugal pump of the invention, in at least one of the bearings disposed at opposite axial ends of the shaft, the radius of curvature of the shaft end ranges from 1.25 mm to 1.5 mm, and the radius of curvature of the bearing surface ranges from 1.5 mm to 2.5 mm. According to this configuration, it is possible to more effectively prevent hemolysis from occurring on a sliding surface between the shaft and the bearing.

In the centrifugal pump, in at least one of the bearings disposed at opposite axial ends of the shaft, the radius of curvature of the shaft end is about 1.5 mm, and a radius of curvature of the bearing is about 2.0 mm. According to this configuration, it is possible to more effectively prevent hemolysis from occurring on the sliding surface between the shaft and the bearing.

In the centrifugal pump, a bearing preload with respect to the shaft in the axial direction may range from about 30 N to about 60 N. According to this configuration, together with the hemolysis prevention effect achieved by setting the radius of curvature as described above, it is possible to more effectively prevent hemolysis from being formed, and it is also possible to prevent a thrombus from being formed and to avoid damage to a bonded portion (e.g., occurrence of a crack, and the like) between a base of the housing and a cover.

In the centrifugal pump, an outer diameter of the impeller may be equal to or greater than 70 mm, and a maximum rotational frequency of the impeller may be equal to or less than 3,000 rpm. According to this configuration, while hemolysis and a thrombus are prevented from being formed, it is still possible to generate comparatively high discharge pressure.

According to the centrifugal pump of the present invention, it is possible to prevent hemolysis from being formed due to sliding between the shaft and the pivot bearing.

DESCRIPTION OF EMBODIMENT

Hereinafter, description will be given regarding a favorable embodiment of a centrifugal pump of the present invention, with reference to the accompanying drawings.

Figure 1:
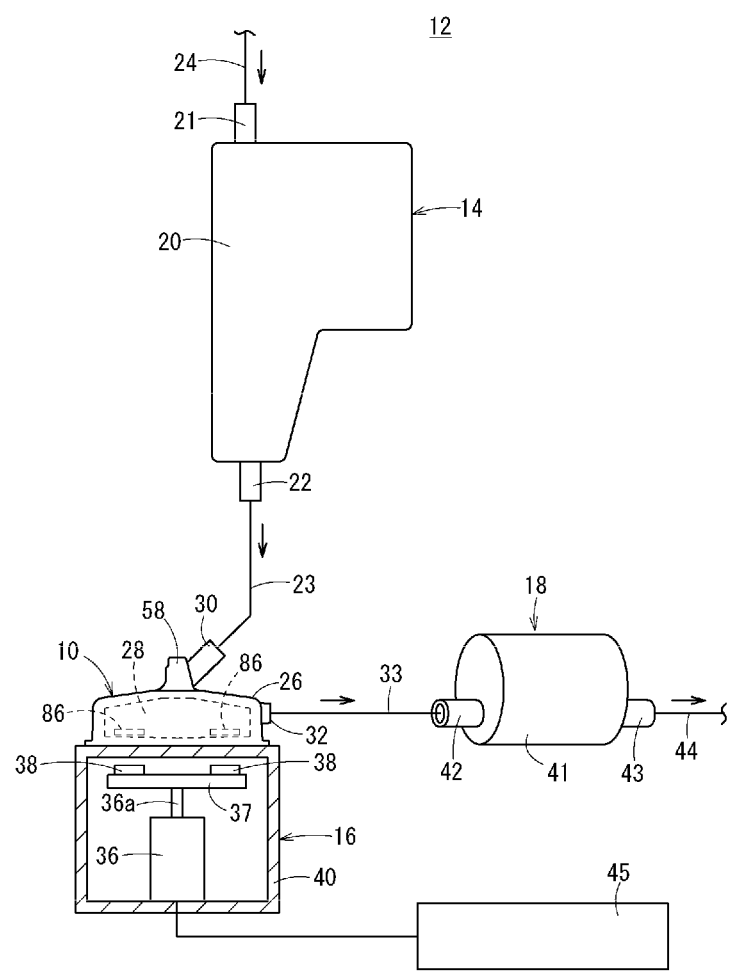
FIG. 1 is a schematic view of a heart-lung machine.

FIG. 1 is a schematic view of a heart-lung machine 12 including a centrifugal pump 10 of the present invention. For example, the heart-lung machine 12 is used for cardiac surgery or the like. The heart-lung machine 12 performs oxygenation of blood drained from a patient, filtering for elimination of foreign bodies, and the like, then returning the blood to the patient. As illustrated in FIG. 1, the heart-lung machine 12 includes a reservoir 14, a centrifugal pump 10, a pump driving unit 16, and a gas exchange unit 18.

The reservoir 14 temporarily stores blood removed from a patient (venous blood). The reservoir 14 has a reservoir main body 20, a blood inlet port 21 which is provided in an upper portion of the reservoir main body 20 and is connected to a venous line 24 for delivering blood from a blood draining cannula inserted into a patient, and a blood outlet port 22 which is provided in a lower portion of the reservoir main body 20 and is connected to the centrifugal pump 10 via a first connection line 23.

Inside the reservoir main body 20, a blood filter (not illustrated) which filters blood flowing in via the blood inlet port 21 is disposed. Note that, the reservoir main body 20 is also provided with an inlet port (not illustrated) which is connected to a cardiotomy line for delivering blood from the surgical field of a patient.

The centrifugal pump 10 delivers blood from the reservoir 14 to the gas exchange unit 18. The centrifugal pump 10 includes at least a housing 26 and an impeller 28 which is rotatably disposed inside the housing 26. The housing 26 has a blood inlet port 30 which is connected to the blood outlet port 22 of the reservoir 14 via the first connection line 23, and a blood outlet port 32 which is connected to the gas exchange unit 18 via a second connection line 33. For example, the first connection line 23 and the second connection line 33 are flexible and transparent tubes.

Blood flowing into a central portion of the impeller 28 through the blood inlet port 30 flows to an outer circumferential side of the impeller 28 while being accelerated in accordance with rotations of the impeller 28, thereby being discharged through the blood outlet port 32. Note that, the detailed structure of the centrifugal pump 10 will be described later.

The pump driving unit 16 has a motor 36, a rotary member 37 (for example, a rotary plate) which is fixed to a rotary shaft 36a of the motor 36, permanent magnets 38 which are attached to the rotary member 37, and a case 40 which accommodates these components. It is preferable that a plurality of the permanent magnets 38 are provided at substantially equal intervals in the circumferential direction centering around the rotary shaft 36a of the motor 36. For example, the permanent magnets 38 are provided as many as the number of the below-described permanent magnets 86 provided in the centrifugal pump 10.

Due to the above-described configuration of the pump driving unit 16, the permanent magnets 38 provided in the pump driving unit 16 magnetically attract the permanent magnets 86 provided in the centrifugal pump 10. When the motor 36 rotates in such a magnetically attracted state, the permanent magnets 38 rotate together with the motor 36, and the impeller 28 also rotates along with the rotations thereof.

Note that, either an AC motor or a DC motor may be used as the motor 36. However, it is preferable to use a variable speed motor. For example, when a stepping motor is used as the motor 36, it is easy to control the flow rate of blood in the centrifugal pump 10.

The heart-lung machine 12 includes a control unit 45, and the control unit 45 controls driving of the motor 36. In the centrifugal pump 10 which is driven as described above, for example, the impeller 28 can rotate within a range from 0 rpm to 3,000 rpm. When the rotational frequency of the impeller 28 is equal to or lower than 3,000 rpm, it is likely to prevent hemolysis and a thrombus from being formed. Note that, the impeller 28 may be able to rotate equal to or higher than 3,000 rpm.

The gas exchange unit 18 has a main body 41, a blood inlet port 42 which is connected to the blood outlet port 32 of the centrifugal pump 10 via the second connection line 33, and a blood outlet port 43 which is connected to a retransfusion line 44 for returning blood to a patient. The main body 41 adds oxygen to blood flowing in via the blood inlet port 42 and performs gas exchange for eliminating carbon dioxide. Note that, the gas exchange unit 18 may also have a function of heat exchange for changing a blood temperature.

Figure 2:
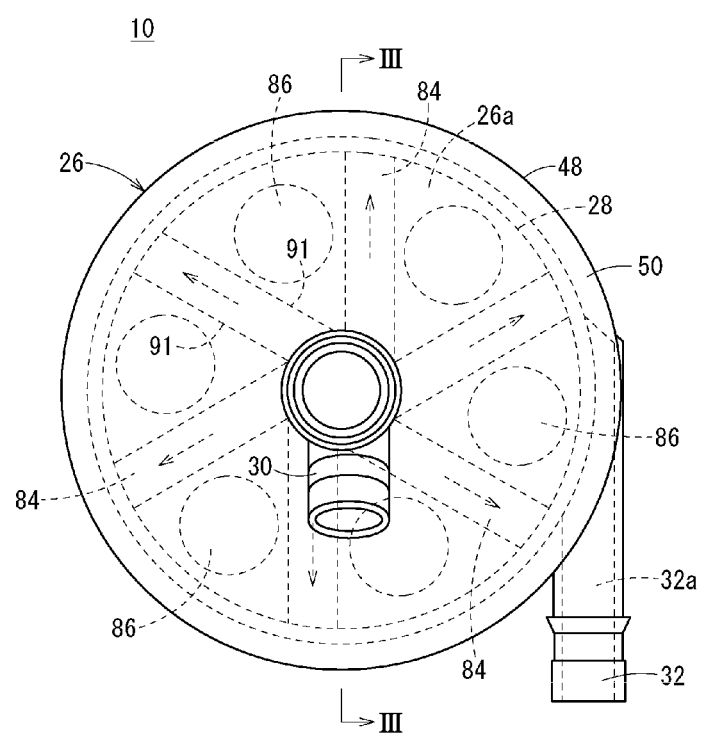
FIG. 2 is a planar view of a centrifugal pump according to an embodiment of the present invention.
Figure 3:
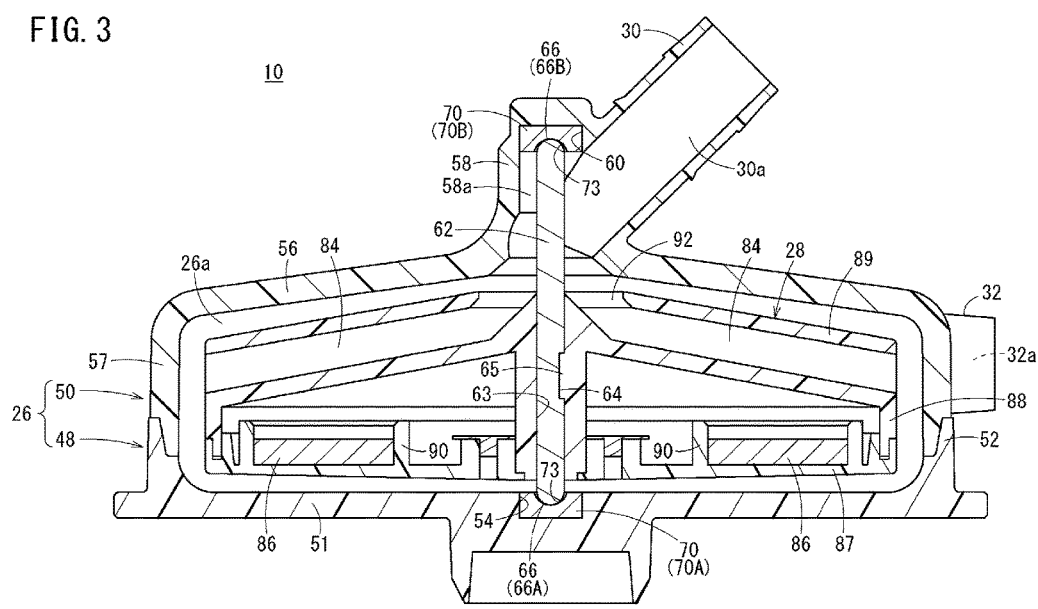
FIG. 3 is a cross-sectional view taken along line III-III in FIG. 2.

FIG. 2 is a planar view of the centrifugal pump 10. FIG. 3 is a cross-sectional view taken along line III-III in FIG. 2.

As illustrated in FIGS. 2 and 3, the housing 26 in the centrifugal pump 10 has a base 48 configuring a lower portion, and a cover 50 configuring an upper portion. The base 48 and the cover 50 form a space 26a (hereinafter, referred to as "the accommodation space 26a") in which the impeller 28 is internally accommodated.

The base 48 has a substantial disk shape in its entirety. As illustrated in FIG. 3, the base 48 has a circular floor 51 and a circumferential wall 52 which protrudes upward from the outer circumferential portion of the floor 51 and continuously encircles the circumference in the circumferential direction. A central portion of the floor 51 is provided with a recessed first disposition portion (i.e., receptacle) 54.

The cover 50 has a disk-shaped ceiling 56 and a circumferential wall 57 which protrudes downward from the outer circumference of the ceiling 56 and continuously encircles the circumference in the circumferential direction. The lower end of the circumferential wall 57 of the cover 50 and the upper end of the circumferential wall 52 of the base 48 are in a state of being fitted with each other and are fixed to each other by appropriate bonding means such as an adhesive and the like. Note that, in FIG. 3, the lower end of the circumferential wall of the cover 50 is fitted with the inner side of the upper end of the circumferential wall of the base 48. However, the upper end of the circumferential wall of the base 48 may be fitted with the inner side of the lower end of the circumferential wall of the cover 50.

The cover 50 is provided with a protruding cylinder portion 58 which protrudes upward from the center of the ceiling 56. The protruding cylinder portion 58 is configured to have a hollow open-bottom structure in which the upper end is closed. Inside an upper portion of the protruding cylinder portion 58, a recessed second disposition portion (i.e., receptacle) 60 is provided.

In addition, the cover 50 is provided with the above-described blood inlet port 30. In the present embodiment, the blood inlet port 30 extends from the protruding cylinder portion 58 in a direction intersecting the protruding cylinder portion 58 (in the illustrated example, in an inclination direction). A lumen 30a of the blood inlet port 30 communicates with the accommodation space 26a via a lumen 58a of the protruding cylinder portion 58.

The cover 50 is also provided with the above-described blood outlet port 32. In the present embodiment, the blood outlet port 32 extends from the outer side surface of the circumferential wall 57 of the cover 50 in a tangential direction. A lumen 32a of the blood outlet port 32 communicates with the accommodation space 26a.

As a configuration material of the housing 26 (the base 48 and the cover 50), for example, it is possible to exemplify various types of resin materials such as various types of glass; polyvinyl chloride; polyethylene; polypropylene; cyclic polyolefin; polystyrene; poly-(4-methylpentene-1); polycarbonate; an acrylic resin; an acrylonitrile-butadiene-styrene copolymer; polyester such as polyethylene terephthalate, polyethylene naphthalate, and the like; a butadiene-styrene copolymer; polyamide (for example, nylon 6, nylon 6,6, nylon 6,10, nylon 12); and the like. It is preferable that the housing 26 is configured to be formed from a transparent material so that blood flowing in the housing 26 can be visually recognized.

In the impeller 28, a plurality of blood induction paths 84 which radially extend from a substantial center of the impeller 28 toward the outer circumferential side are provided. In addition, inside the impeller 28, a plurality of the permanent magnets 86 for transmitting rotating force to the impeller 28 from the outside are provided at substantially equal intervals in the circumferential direction. The blood induction paths 84 are not limited to being straight as illustrated in FIG. 2 and may have curved shapes.

The outer diameter of the impeller 28 is not particularly limited. However, for example, the outer diameter can be set to range approximately from 50 mm to 100 mm. As the outer diameter of the impeller 28 becomes greater, it is more likely to generate high discharge pressure. For example, when the outer diameter of the impeller 28 is equal to or greater than 70 mm, even though the maximum rotational frequency is approximately 3,000 rpm, it is possible to generate comparatively high discharge pressure. As described above, in a case where the rotational frequency is equal to or less than 3,000 rpm, it is likely to prevent hemolysis and a thrombus from being formed. Therefore, when the outer diameter is preferably equal to or greater than 70 mm and the maximum rotational frequency is equal to or less than 3,000 rpm, while preventing hemolysis and a thrombus from being formed, the impeller 28 can generate comparatively high discharge pressure.

In the present embodiment, the impeller 28 has a first rotor 87 which is configured to form the bottom portion, a second rotor 88 which concentrically overlaps the first rotor 87 from above, and a rotor cover 89 which concentrically overlaps the second rotor 88 from above.

The plurality of above-described permanent magnets 86 are respectively held by a plurality of magnet holding portions 90 which are provided on the top surface of the first rotor 87. The plurality of above-described blood induction paths 84 are formed between the second rotor 88 and the rotor cover 89. A plurality of flow channel forming walls 91 which protrude downward from the bottom surface of the rotor cover 89 are configured to form both side walls of the blood induction paths 84. The top surface of the rotor cover 89 has a conical shape, and an opening 92 is formed in a central portion thereof.

A shaft 62 is provided at the central rotational axis of the impeller 28. The shaft 62 is a straight rod-shaped member and has spherically-shaped shaft ends 66 at opposed axial ends. The shaft 62 is fixed to the impeller 28 in a state of being inserted into the insertion hole (i.e., bore) 63 penetrating the central axis of the impeller 28 in the axial direction. The shaft 62 and the impeller 28 cannot relatively rotate and are fixed to each other in a state of not being able to be relatively displaced in the axial direction. In the present embodiment, a projection 65 which is provided on the inner circumferential wall forming the insertion hole 63 of the impeller 28 engages with a matching groove 64 which is provided in the shaft 62. Thus, the shaft 62 and the impeller 28 are fixed to each other.

The opposing ends of the shaft 62 respectively protrude downward and upward from the impeller 28. Hereinafter, to discriminate the two shaft ends 66 from each other, the shaft end 66 on the lower side is referred to as "the first shaft end 66A" and the shaft end 66 on the upper side is referred to as "the second shaft end 66B".

For example, the configuration material of the shaft 62 can be selected from the materials exemplified above as the configuration material of the housing 26. For example, it is preferable that the shaft 62 is configured to be formed from a ceramic-based material such as alumina ceramic and the like being excellent in abrasion resistance and sliding properties.

The centrifugal pump 10 also includes bearings 70 which are provided at opposite ends of the shaft 62 and respectively and pivotally support the shaft ends 66. Hereinafter, to discriminate the two bearings 70 from each other, the bearing on the lower side, that is, the bearing pivotally supporting the first shaft end 66A is referred to as "the first bearing 70A", and the bearing on the upper side, that is, the second bearing 70B pivotally supporting the second shaft end 66B is referred to as "the second bearing 70B". In other words, the first bearing 70A and the second bearing 70B are configured to be pivot bearings.

Figure 4:
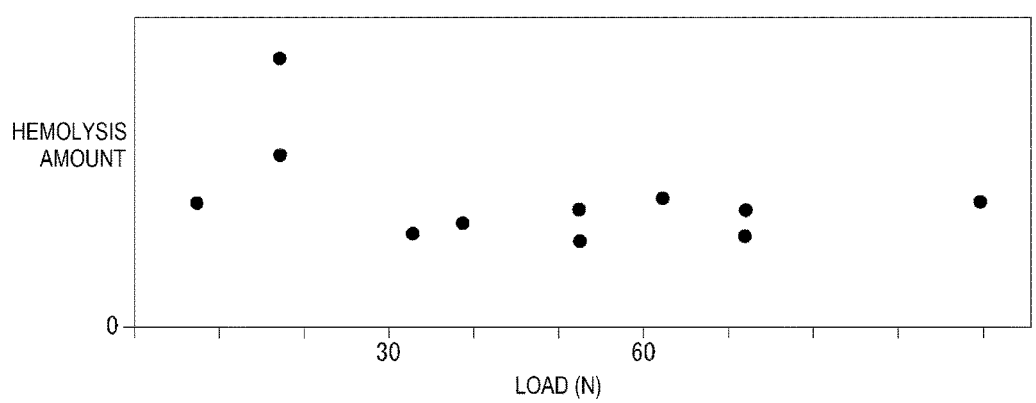
FIG. 4 is a graph illustrating relationships between bearing preloads and amount(volume) of hemolysis.

The shaft 62 is rotatably held between the first bearing 70A and the second bearing 70B in a state where a predetermined bearing preload is applied in the axial direction inside the housing 26. In a case where the bearing preload is excessively small (for example, in a case of being smaller than 30 N), oscillations during rotations of the shaft 62 increase so that hemolysis is more likely to occur. FIG. 4 is a graph illustrating relationships between the bearing preloads and an amount(volume) of hemolysis, obtained through a test. As seen from FIG. 4, in a case where the bearing preload is smaller than 30 N, compared to a case of being equal to or greater than 30 N, it is ascertained that the hemolytic dose increases remarkably.

On the contrary, in a case where the bearing preload with respect to the shaft 62 is significantly higher (for example, in a case of exceeding 60 N), a thrombus is likely to occur, and there is a possibility of damage to a bonded portion between the base 48 of the housing 26 and the cover 50. Therefore, it is preferable that the bearing preload applied to the shaft 62 is set within a proper range (for example, approximately from 30 N to 60 N) when manufacturing the centrifugal pump 10.

Figure 5:
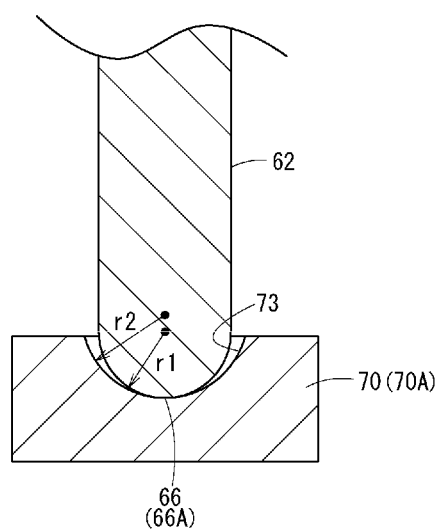
FIG. 5 is an enlarged cross-sectional view of a shaft and a first bearing.

The first bearing 70A has a bearing surface 73 which is recessed so as to have a spherical surface shape. The bearing surface 73 of the first bearing 70A comes into contact with the first shaft end 66A. As illustrated in FIG. 5, a radius r2 of curvature of the bearing surface 73 of the first bearing 70A is greater than a radius r1 of curvature of the first shaft end 66A. The first bearing 70A is disposed in the recessed first disposition portion 54 which is provided in a central portion of the base 48.

In the present embodiment, a ratio of the radius r1 of curvature of the first shaft end 66A with respect to the radius r2 of curvature of the bearing surface 73 of the first bearing 70A is set to be equal to or less than 85%, and is more preferably set to be equal to or less than 75%. In this case, the radius r1 of curvature of the first shaft end 66A and the radius r2 of curvature of the bearing surface 73 of the first bearing 70A can be respectively set to 1.5 mm and 2.0 mm, for example (the ratio of the radius r1 of curvature of the first shaft end 66A with respect to the radius r2 of curvature of the bearing surface 73 of the first bearing 70A is 75%).

The second bearing 70B has a different bearing surface 73 which is recessed so as to have a spherical surface shape. The bearing surface 73 of the second bearing 70B comes into contact with the second shaft end 66B, and the radius of curvature thereof is greater than the radius of curvature of the second shaft end 66B. In the present embodiment, the radius of curvature of the second shaft end 66B is the same as the radius r1 of curvature of the first shaft end 66A (refer to FIG. 5), and the radius of curvature of the bearing surface 73 of the second bearing 70B is the same as the radius r2 of curvature of the bearing surface 73 of the first bearing 70A (refer to FIG. 5). The second bearing 70B is disposed in the recessed second disposition portion 60 which is provided in the protruding cylinder portion 58 of the cover 50.

For example, the configuration material of the bearings 70 can be selected from the materials exemplified above as the configuration material of the housing 26. It is preferable that the configuration material of the bearings 70 is configured to be formed from polyethylene having an ultra-high molecular weight and being excellent in abrasion resistance and self-lubrication properties.

In the centrifugal pump 10 having the above-described configuration, when blood flows into the housing 26 via the blood inlet port 30, the blood flows into the impeller 28 through the opening 92 provided at the apex portion of the impeller 28, thereby being scattered. Centrifugal force is applied to the scattered blood due to rotations of the impeller 28 so that the blood flows inside the blood induction paths 84 toward the outer circumferential side of the impeller 28. The blood flowing out from the blood induction paths 84 flows between the outer side surface of the impeller 28 and the inner side surface of the housing 26. Thereafter, the blood flows out through the blood outlet port 32.

The centrifugal pump 10 according to the present embodiment basically has a configuration as described above. Hereinafter, an operation and an effect thereof will be described.

As described above, in the centrifugal pump 10 according to the present embodiment, both the ratio of the radius r1 of curvature of the first shaft end 66A with respect to the radius r2 of curvature of the bearing surface 73 of the first bearing 70A and the ratio of the radius of curvature of the second shaft end 66B with respect to the radius of curvature of the bearing surface 73 of the second bearing 70B are set to equal to or less than 85%. Accordingly, gaps between the shaft ends 66 of the shaft 62 and the bearing surfaces 73 of the bearings 70 become suitable in size. Therefore, it is possible to prevent hemolysis from occurring due to sliding between the shaft 62 and the bearings 70.

In order to check the above-described effect of the present invention, a test has been executed. In the test, in 15 mL of blood put in a container, while the shaft was axially compressed with a bearing preload of 40 N with respect to each of the bearings respectively corresponding to the Novel Example and Conventional Controls 1 to 4 illustrated in FIGS. 6A to 6E, the shaft was continuously rotated for an hour at a rotational frequency of 3,000 rpm. In all the shafts used in the experiments, the outer diameter was 3.0 mm and the radius of curvature of the shaft end was 1.5 mm.

Figure 6A:
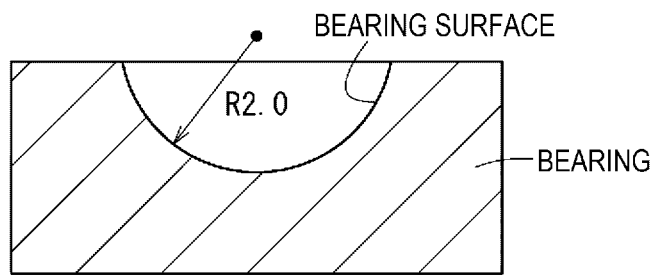
FIG. 6A is a cross-sectional view of a bearing according to a Novel Example of the present invention.
Figure 6B:
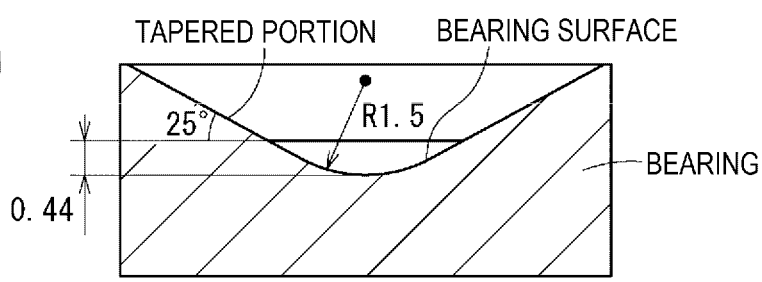
FIG. 6B is a cross-sectional view of a bearing according to Conventional Control 1.
Figure 6C:
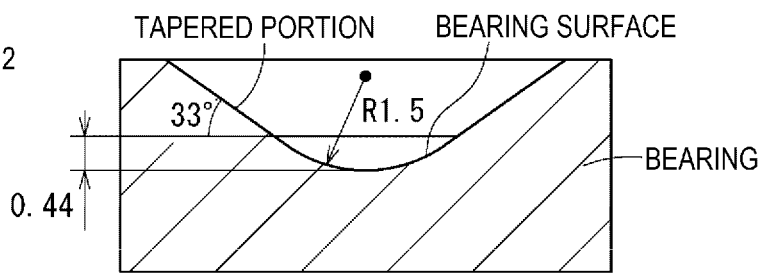
FIG. 6C is a cross-sectional view of a bearing according to Conventional Control 2.
Figure 6D:
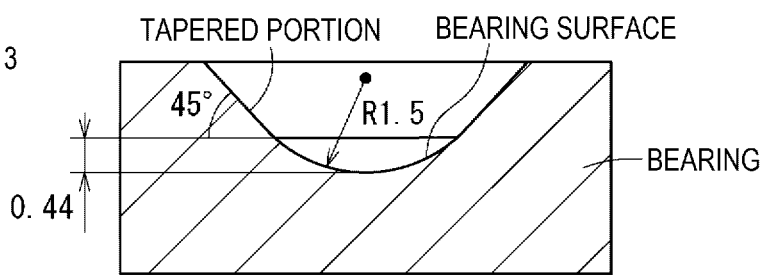
FIG. 6D is a cross-sectional view of a bearing according to Conventional Control 3.
Figure 6E:
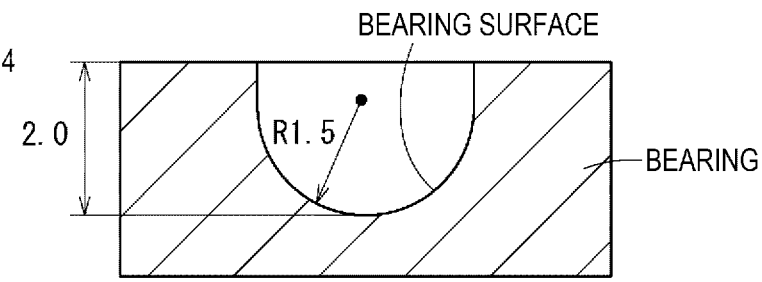
FIG. 6E is a cross-sectional view of a bearing according to Conventional Control 4.

As illustrated in FIG. 6A, in the bearing of the Novel Example, the radius of curvature of the bearing surface was 2.0 mm. Accordingly, the ratio of the radius of curvature of the shaft end of the shaft with respect to the radius of curvature of the bearing surface was 75%.

As illustrated in FIGS. 6B to 6E, in the bearings of Conventional Control examples 1 to 4, the radius of curvature of the bearing surface was 1.5 mm. Accordingly, the ratio of the radius of curvature of the shaft end of the shaft with respect to the radius of curvature of the bearing surface was 100%. However, in Conventional Controls 1 to 3, the depth of the bearing surface was 0.44 mm which was smaller than the radius of curvature (1.5 mm) of the shaft end of the shaft. A tapered portion was provided on the periphery of the bearing surface. The angles of the tapered portion in Conventional Controls 1 to 3 were respectively 25°, 33°, and 45°. In addition, in Conventional Control 4, the depth of the bearing surface was 2.0 mm which was greater than the radius of curvature of the shaft end of the shaft.

As a result of the test performed under the above-described conditions, hemolysis was effectively prevented in the Novel Example. Therefore, compared to Conventional Control 1 to 4, it was confirmed that the amount(volume) of hemolysis was drastically small. It is considered that such an effect of preventing hemolysis is achieved due to the gap retained in a suitably wide manner between the shaft end of the shaft and the bearing surface of the bearing.

Meanwhile, in Conventional Controls 1 to 3, as the angle of the tapered portion became smaller, that is, as the gap between the shaft and the bearing became greater, it was confirmed that the amount(volume) of hemolysis decreased. Nevertheless, the amount(volume) of hemolysis was greater than that of the Novel Example, and no particularly meaningful effect in terms of hemolysis prevention was observed. In Conventional Control 4, it was confirmed that the amount (volume) of hemolysis increased remarkably. Regarding the case of Conventional Control 4, it is considered to be caused by the fact that the bearing surface in its entirety comes into contact with the shaft.

Figure 7A:
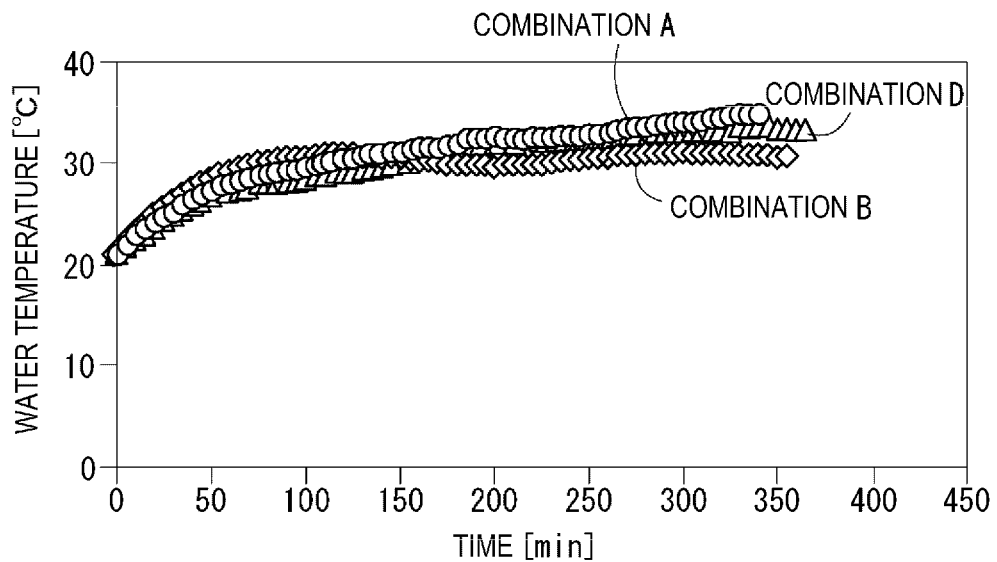
FIG. 7A is a graph illustrating an experimental result related to heat generation during rotations of the shaft.
Figure 7B:
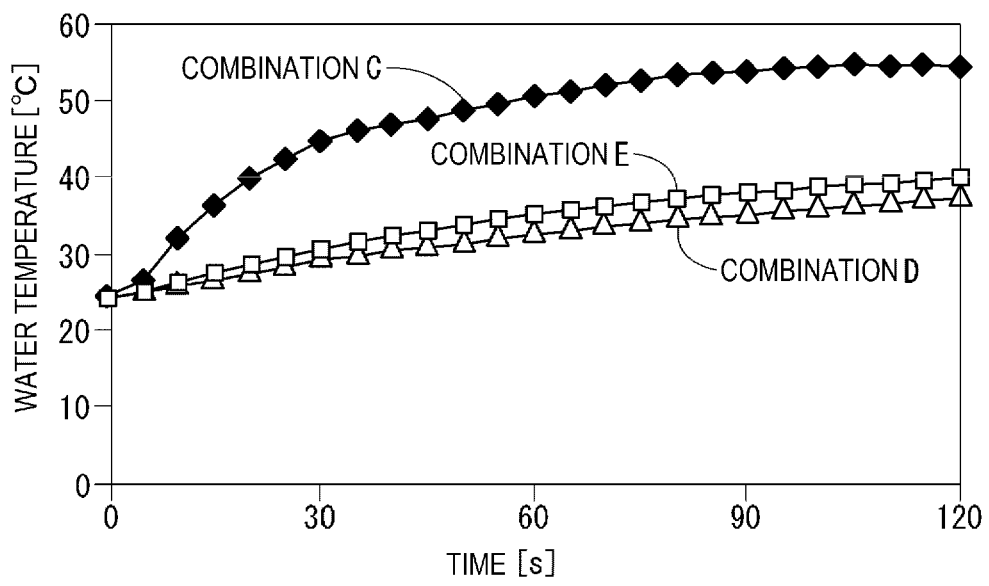
FIG. 7B is another graph illustrating the experimental result related to heat generation during rotations of the shaft.

FIGS. 7A and 7B illustrate the experimental results related to the calorific values during rotations of the shaft, in each of the combinations (A to E) of the shafts and the bearings of which the radii of curvature are formed as shown in the following Table 1.

TABLE 1

| Combinations | Radius of Curvature of Shaft End of Shaft (mm) | Radius of Curvature of Bearing Surface (mm) | Ratio of Radius of Curvature (%) |
|---|---|---|---|
| A | 1.25 | 1.5 | Approximately 83 |
| B | 1.25 | 2.0 | Approximately 63 |
| C | 1.5 | 1.5 | 100 |
| D | 1.5 | 2.0 | 75 |
| E | 1.5 | 2.5 | 60 |

In this test, in 9 mL of fluid volume of water, while the shaft was pressed with an axial preload of approximately 52 N (5.3 kgf) with respect to the bearing, the shaft was continuously rotated for a predetermined period of time at a rotational frequency of 2,500 rpm, and the temperature rise of water was measured. The room temperature was maintained at 25° C. Note that, in Table 1, "Ratio of Radius of Curvature (%)" denotes the ratio (%) of the radius of curvature of the shaft end of the shaft with respect to the radius of curvature of the bearing surface.

As illustrated in FIGS. 7A and 7B, in the combination C, the temperature rise due to the elapse of time was significant, that is, the calorific value was great. In the combinations A, B, D, and E, compared to the combination C, a result of a gentle temperature rise due to the elapse of time, that is, a small calorific value was obtained. Incidentally, the combination C having a great calorific value corresponds to Conventional Control 4 of FIG. 6E, and the combination D having a small calorific value corresponds to the Novel Example of FIG. 6A. From the above-referenced fact, it is considered that formation of hemolysis is greatly influenced by heat generation.

According to the test results thereof, in a case where the ratio of the radius of curvature of the shaft end of the shaft with respect to the radius of curvature of the bearing surface ranges from 60% to approximately 83%, it is ascertained that heat generation can be prevented and a hemolysis prevention effect can be obtained. In addition, from the fact that almost no difference was recognized between the calorific values (temperature rises) through the comparison between the ratio of 75% (combination D) and the ratio of approximately 83% (combination A), it is considered that even though the ratio is approximately 85%, a hemolysis prevention effect can be obtained.

Note that, another experiment (not illustrated) was performed so as to measure the amount(volume) of hemolysis with the combination of a flat bearing surface and a spherically-shaped shaft end (in this case, the radius of curvature of the shaft end was 1.5 mm), and the calorific value became the least in a case of this combination. From the above-referenced fact, even in a case where the ratio is less than 60%, it is ascertained that an effect of preventing hemolysis caused by heat generation can be obtained. However, in a case where the ratio of the radius of curvature of the shaft end of the shaft with respect to the radius of curvature of the bearing surface is less than 60% (for example, flat bearing surface), the surface does not function as a bearing. Accordingly, shaft shaking or vibrations caused by rotations are likely to occur, and thus, formation of hemolysis caused by shaft shaking or vibrations is likely to occur. Therefore, from the viewpoint of an occurrence of shaft shaking or vibrations caused by rotations, it is preferable that the ratio of the radius of curvature of the shaft end of the shaft with respect to the radius of curvature of the bearing surface is equal to or greater than 60%. Therefore, a method in which shaft shaking or vibrations caused by rotations are prevented and absorbed without hindering rotations is required.

As it has been understood from the above-described fact, according to the present invention, when a relationship between the radius of curvature of the shaft end 66 of the shaft 62 and the radius of curvature of the bearing surface 73 of the bearings 70 (the ratio of the radius of curvature of the shaft end 66 with respect to the radius of curvature of the bearing surface 73) is set within a predetermined range (equal to or less than 85%), the gap between the shaft end 66 of the shaft 62 and the bearing surface 73 of the bearings 70 becomes suitable in size. Accordingly, it is possible to prevent hemolysis from occurring due to sliding between the shaft 62 and the bearings 70.

In addition, with reference to the experimental results, in addition to setting of the ratio related to the radius of curvature, when the radius of curvature of the shaft end 66 is set to range from 1.25 mm to 1.5 mm, or the radius of curvature of the bearing surface 73 is set to range from 1.5 mm to 2.5 mm, it is possible to effectively prevent hemolysis from occurring due to sliding between the shaft 62 and the bearings 70.

In addition, as is clear from the experimental results, when the radius of curvature of the first shaft end 66A (or the second shaft end 66B) is set to be 1.5 mm and the radius of curvature of the bearing surface 73 of the first bearing 70A (or the second bearing 70B) is set to be 2.0 mm, it is possible to reliably prevent hemolysis from occurring due to sliding between the shaft 62 and the bearings 70.

In addition, when the bearing preload in the axial direction with respect to the shaft 62 is set to a range from 30 N to 60 N, together with the above-described hemolysis prevention effect obtained by setting the radius of curvature, it is possible to more effectively prevent hemolysis from being formed, and it is possible to prevent formation of a thrombus and damage to the bonded portion (an occurrence of a crack, and the like) between the base 48 of the housing 26 and the cover 50.

Note that, the ratio of the radius r1 of curvature of the first shaft end 66A with respect to the radius r2 of curvature of the bearing surface 73 of the first bearing 70A may be different from the ratio of the radius of curvature of the second shaft end 66B with respect to the radius of curvature of the bearing surface 73 of the second bearing 70B.

In the above-described embodiment, an example in which both the ratio of the radius r1 of curvature of the first shaft end 66A with respect to the radius r2 of curvature of the bearing surface 73 of the first bearing 70A and the ratio of the radius of curvature of the second shaft end 66B with respect to the radius of curvature of the bearing surface 73 of the second bearing 70B are equal to or less than 85% is illustrated. However, the present invention is not limited thereto. Therefore, for example, any one between the ratio of the radius r1 of curvature of the first shaft end 66A with respect to the radius r2 of curvature of the bearing surface 73 of the first bearing 70A and the ratio of the radius of curvature of the second shaft end 66B with respect to the radius of curvature of the bearing surface 73 of the second bearing 70B may be equal to or less than 85%. In this case as well, it is possible to prevent hemolysis from being formed.

In the above description, preferred embodiments of the present invention has been exemplified. However, the present invention is not limited to the embodiment, and it is not necessary to mention that various modifications and changes can be made without departing from the scope of the present invention.

What is claimed is:
1. A centrifugal pump comprising:
a housing;
an impeller rotatably disposed inside the housing;
a shaft fixed to the impeller at a central rotational axis and having spherically-shaped axial ends each with a respective radius of curvature; and
first and second bearings having spherically-shaped bearing surfaces, respectively, each with a respective radius of curvature and pivotally supporting a respective shaft axial end;
wherein the shaft axial ends are in continuous contact with the first and second bearings to provide a bearing preload with respect to the shaft in a range from 30 N to 60 N; and
wherein a ratio of the radius of curvature of one of the shaft ends with respect to the radius of curvature of the respective bearing surface is equal to or less than 85% and is equal to or greater than 60%.

2. The centrifugal pump according to claim 1,
wherein the radius of curvature of at least one of the shaft ends ranges from 1.25 mm to 1.5 mm, and the radius of curvature of the respective bearing surface ranges from 1.5 mm to 2.5 mm.

3. The centrifugal pump according to claim 1,
wherein the radius of curvature of at least one of the shaft ends is 1.5 mm, and the radius of curvature of the respective bearing is 2.0 mm.

4. The centrifugal pump according to claim 1,
wherein an outer diameter of the impeller is equal to or greater than 70 mm, and
wherein a maximum rotational frequency of the impeller is equal to or less than 3,000 rpm.

5. The centrifugal pump according to claim 1,
wherein the radius of curvature of each of the shaft ends are equal, and the radius of curvature of each of the respective bearing surfaces are equal.

\* \* \* \* \*